(12) United States Patent
Zhang et al.

(10) Patent No.: US 8,668,649 B2
(45) Date of Patent: Mar. 11, 2014

(54) SYSTEM FOR CARDIAC STATUS DETERMINATION

(75) Inventors: Hongxuan Zhang, Palatine, IL (US); Prabhu Mukundhan, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 439 days.

(21) Appl. No.: 12/907,136

(22) Filed: Oct. 19, 2010

(65) Prior Publication Data

US 2011/0190643 A1 Aug. 4, 2011

Related U.S. Application Data

(60) Provisional application No. 61/301,338, filed on Feb. 4, 2010.

(51) Int. Cl.
*A61B 5/02* (2006.01)

(52) U.S. Cl.
USPC .......................... 600/485; 600/481

(58) Field of Classification Search
USPC .................. 600/300–301, 485–499, 481
See application file for complete search history.

(56) References Cited

U.S. PATENT DOCUMENTS

| | | | |
|---|---|---|---|
| 4,566,463 A | 1/1986 | Taniguchi et al. | |
| 4,862,361 A * | 8/1989 | Gordon et al. | 600/450 |
| 5,279,303 A | 1/1994 | Kawamura et al. | |
| 5,615,684 A | 4/1997 | Hagel et al. | |
| 5,752,919 A | 5/1998 | Schrimpf | |
| 6,050,951 A | 4/2000 | Friedman et al. | |
| 6,117,075 A | 9/2000 | Barnea | |
| 6,224,553 B1 | 5/2001 | Nevo | |
| 6,251,081 B1 * | 6/2001 | Narimatsu | 600/490 |
| 6,308,098 B1 | 10/2001 | Meyer | |
| 6,485,429 B2 | 11/2002 | Forstner | |
| 6,490,480 B1 | 12/2002 | Lerner | |
| 6,511,436 B1 | 1/2003 | Asmar | |
| 6,616,613 B1 | 9/2003 | Goodman | |
| 6,923,769 B2 * | 8/2005 | Nishii et al. | 600/485 |
| 6,929,610 B2 | 8/2005 | Forstner | |
| 7,074,192 B2 | 7/2006 | Friedman et al. | |
| 7,367,949 B2 | 5/2008 | Korhonen et al. | |
| 7,374,541 B2 | 5/2008 | Amitzur et al. | |
| 7,384,395 B2 | 6/2008 | Hatlestsad et al. | |
| 7,413,548 B2 | 8/2008 | Tadokoro et al. | |

(Continued)

OTHER PUBLICATIONS

Jobbagy, et al. "Blood Pressure Measurement at Home." World Congress on Medical Physics and Biomedical Engineering. 2007. vol. 14, part 22. pp. 3453-3456.*

(Continued)

*Primary Examiner* — Patricia Mallari
*Assistant Examiner* — Tiffany Weston
(74) *Attorney, Agent, or Firm* — Brennan K Bradley

(57) ABSTRACT

A system improves detection and diagnosis of blood pressure based cardiac function and tissue activities by analyzing and characterizing cardiac blood pressure signals (including non-invasive and invasive blood pressure, discrete values and continuous waveforms) using pressure signal variation and variability calculation and evaluation. The system combines blood pressure analysis with multi clinical related factors and parameters to detect and quantify cardiac health status and arrhythmia severity. The system determines an accurate time, location and severity of cardiac pathology and events by calculating blood pressure variability and statistical variation. The accurately and reliably identifies cardiac disorders, differentiates cardiac arrhythmias, characterizes pathological severity, predicts the life-threatening events, and supports evaluation of drug delivery effects.

18 Claims, 9 Drawing Sheets

(56) References Cited

U.S. PATENT DOCUMENTS

2006/0287605 A1* 12/2006 Lin et al. .................. 600/521
2007/0179769 A1* 8/2007 Grichnik et al. ............ 703/11
2008/0058890 A1* 3/2008 Tang et al. ................. 607/44

OTHER PUBLICATIONS

Coefficient of Variation—Wikipedia.*

Normalization—Wikipedia.*

Nafz et al., "Endogenous Nitric Oxide Buffers Blood Pressure Variability Between 0.2 and 0.6 Hz in the Conscious Rat", American Journal of Physiology (Hearth Circulation Physiology), 272: H632-H637, 1997.

K. Laederach-Hofmann et al., "Early autonomic dysfunction in patients with diabetes mellitus assessed by spectral analysis of heart rate and blood pressure variability", Clinical Physiology, vol. 19, No. 2: 97-106, 1999.

Parati et al., "Neural cardiovascular regulation and 24-hour blood pressure and heart rate variability", Annals of the New York Academy of Sciences. 783:47-63, 1996.

Pelat et al., "Rosuvastatin Decreases Caveolin-1 and Improves Nitric Oxide-Dependent Heart Rate and Blood Pressure Variability in Apolipoprotein E−/− Mice In Vivo", Circulation, 107: 2480-2486, 2003.

* cited by examiner

SYSTEM FOR CARDIAC STATUS DETERMINATION

This is a non-provisional application of provisional application Ser. No. 61/301,338 filed Feb. 4, 2010, by H. Zhang et al.

FIELD OF THE INVENTION

This invention concerns a system for heart performance characterization and abnormality detection, by analyzing sampled data values representing patient blood pressure occurring during individual heart cycles of multiple sequential heart cycles.

BACKGROUND OF THE INVENTION

Blood pressure (BP) measures force applied to the walls of arteries as a heart pumps blood through the body. The pressure is determined by the force and amount of blood pumped, and the size and flexibility of the arteries. Systolic and diastolic arterial BP is not static but undergoes natural variations from one heartbeat to another and throughout the day (in a circadian rhythm). Blood pressure variation and changes may be utilized for patient health status monitoring. Some recent studies successfully use power spectra (such as indicating Low or High Frequency bandwidth) to analyze blood pressure variability for detecting cardiac abnormality. However, blood pressure variability may be affected by many factors, such as age, disease, breathing control, physical conditions and neurological status.

There are two types of blood pressure: systolic and diastolic. Systolic blood pressure comprises pressure of the blood when the heart has imparted the maximum pressure. Diastolic blood pressure is the pressure when the heart is in the resting phase. Blood pressure (BP) is the pressure exerted by circulating blood on the walls of blood vessels, and is a principal vital sign. During each heartbeat, BP varies between a maximum (systolic) and a minimum (diastolic) pressure. The mean BP decreases as the circulating blood moves away from the heart through arteries and has its greatest decrease in the small arteries and arterioles, and continues to decrease as the blood moves through the capillaries and back to the heart through veins. The systolic pressure and diastolic pressure may show different kinds of variation and trends for different cardiac events or arrhythmias and pressure mean value may not detect cardiac conditions.

Noninvasive auscultatory and oscillometric measurements are simpler and quicker than invasive measurements have virtually no complications, and are less unpleasant and painful for the patient. However, noninvasive methods may yield lower accuracy and small systematic differences in numerical results. Non-invasive measurement methods are more commonly used for routine examinations and monitoring. Systolic and diastolic arterial BPs change in response to stress, nutritional factors, drugs, disease, exercise, and momentarily from standing up. Sometimes the variations are large. Hypertension refers to arterial pressure being abnormally high, as opposed to hypotension, when it is abnormally low. Along with body temperature, respiratory rate, and pulse rate, BP measurements are the most commonly measured physiological parameters. However known pressure data analysis typically fails to comprehensively extract pathology related pressure information and exclude non-pathology data and noise. This results in a high rate of false alarm in cardiac pathology detection.

Known blood pressure analysis usually tracks the absolute value of systolic and diastolic blood pressure measurements and mean calculations discretely (e.g., Measuring Non-invasive blood pressure every 5 minutes), which may fail to extract sufficient pathology and event information. Known pressure analysis may also fail to exclude noise factors (non-related pressure variation factors, such as respiration) which may distort detection and characterization accuracy of cardiac events or arrhythmias. Further, known blood pressure analysis usually does not differentiate the results of different pressure analysis, such as systolic, diastolic, EoS (end of systolic pressure), EoD (end of diastolic pressure) and fail to bridge cardiac arrhythmia diagnosis and status characterization with pressure calculation based multi-parameter analysis. A system according to invention principles addresses these deficiencies and related problems.

SUMMARY OF THE INVENTION

A system improves detection and diagnosis of blood pressure based cardiac function and tissue activities by analyzing and characterizing cardiac blood pressure signals (including non-invasive and invasive blood pressure, discrete values and continuous waveforms) involving determining pressure signal variation and calculated parameter variability. A system for heart performance characterization and abnormality detection includes an interface for receiving a set of sampled data values representing patient blood pressure occurring during individual heart cycles of multiple sequential heart cycles. A signal processor generates a mathematical distribution using the received sampled data set and calculates, (a) a first value substantially comprising an average of the sampled data set, (b) second value substantially comprising a distribution value at a first deviation point from the average of the data set and (c) a ratio of the first and second value as a representation of blood pressure variation. A comparator compares the ratio with a threshold value to provide a comparison indicator. A patient monitor in response to the comparison indicator indicating the ratio exceeds the threshold value, generates an alert message associated with the threshold.

DETAILED DESCRIPTION OF THE INVENTION

A system improves detection and diagnosis of blood pressure based cardiac function and tissue activities by analyzing and characterizing cardiac blood pressure signals (including non-invasive and invasive blood pressure, discrete values and continuous waveforms) using pressure signal variation and variability calculation. The system combines blood pressure analysis with multi clinical related factors and parameters to detect and quantify cardiac health status and arrhythmia severity. The system determines an accurate time, location and severity of cardiac pathology and events by calculating blood pressure variability and statistical variation. The system identifies cardiac disorders, differentiates cardiac arrhythmias, characterizes pathological severity, predicts life-threatening events, and supports evaluation of drug delivery effects.

The system performs blood pressure variation analysis involving analyzing different pressure values, such as systolic, diastolic, EoS (end of systolic pressure), EoD (end of diastolic pressure) values, to provide information for cardiac status and event detection and interpretation. The system employs different kinds of factors (patient information, medical history) and synchronizes information (respiration, ECG) to improve pressure based pathology detection and characterization. An ANN (artificial neural network), fuzzy model or expert system, may be used for data combination and analysis for pathology diagnosis. Different types of pressure value and variation in the values have different value ranges and may reflect different kinds of pathologies. Diastolic pressure (higher than 90 mm Hg) indicates hypertension, systolic pressure (lower than 90 mm Hg) indicates low blood pressure, for example. The blood pressure analysis may be utilized for earlier detection, diagnosis and characterization of cardiac events and arrhythmias.

Blood pressure data is often corrupted and the system facilitates elimination of electrical noise, patient movement-noise (respiration, physical movement). System pressure data variation calculation is used for, non-invasive (NIBP) and invasive (intra-cardiac and other least invasive measurement) blood pressure analysis as well as analysis of pressure from different portions of the body, such as heart, arteries, veins, or other parts of the body. Different kinds of pressure variation are used to track cardiac pathologies and events of patients. In combination with other data (such as age, patient history, respiration, pulse rate, ECG signal, SPO2 signal data), the system excludes non-pathological factors from pressure analysis, which facilitates cardiac status tracking, detection and characterization. Blood pressure is continually changing depending on activity, temperature, diet, emotional state, posture, physical state, and medication use and these factors are accommodated by system analysis.

Figure 1:
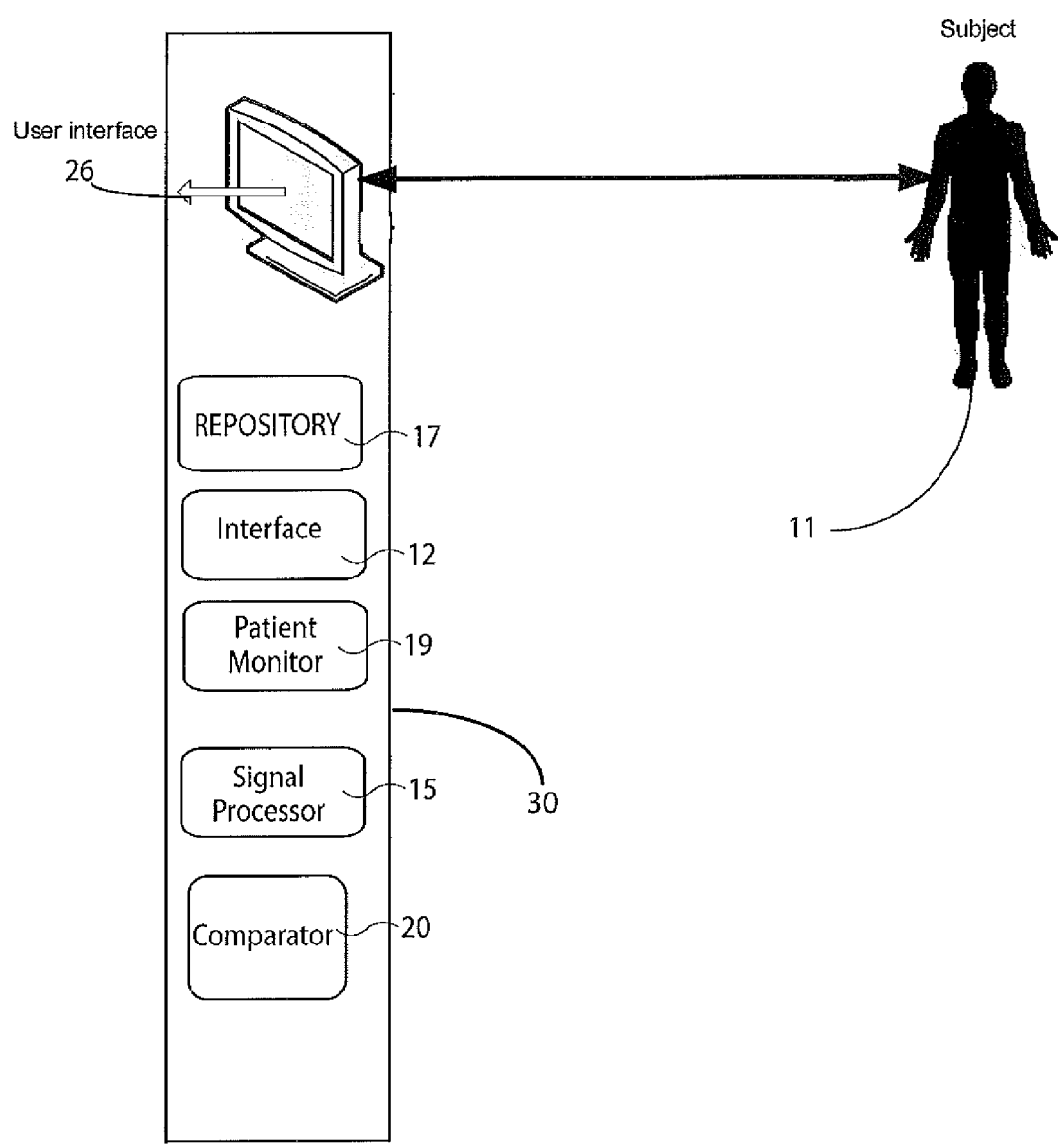
FIG. 1 shows a system for heart performance characterization and abnormality detection, according to invention principles.

FIG. 1 shows system 10 for heart performance characterization and abnormality detection. Hemodynamic signals, such as invasive and non-invasive blood pressure waveforms and related waveform calculations (such as dP/dt, differential of blood pressure), are used by system 10 to diagnose, evaluate and quantitatively characterize heart function, arrhythmias, and patient health status. NIBP measurement of an arm is typically utilized for patient health status detection and characterization, especially in noisy cases (for example, in an ICD installation, ECG signals are noisy and contain artifacts). However, NIBP data provides systolic, diastolic, mean pressure values (discrete numbers) at intervals of a couple minutes for example (typically 5 minutes). System 10 provides more specific and detailed blood pressure analysis to continuously monitor and quantify the status and health of medical patients. System 10 determines variation and variability of blood pressure data for tracking abnormality of cardiac health and arrhythmias. The system determines variation and variability of blood pressure measurements and performs multi-parameter analysis by using a combination of information for patient status determination and prediction.

FIG. 1 shows system 10 for heart performance characterization and abnormality detection. System 10 comprises at least one computer system, workstation, server or other processing device 30 including interface 12, repository 17, patient monitor 19, signal processor 15, comparator 20 and a user interface 26. Interface 12 receives a set of sampled data values representing blood pressure of patient 11 occurring during individual heart cycles of multiple sequential heart cycles. Signal processor 15 generates a mathematical distribution (e.g., a Gaussian distribution, a normal distribution, an Autoregression distribution model and an Autoregression and Moving Average distribution model) using the received sampled data set and calculates a first value, second value and ratio of the first and second value. The first value substantially comprises an average of the sampled data set, the second value substantially comprises a distribution value at a first deviation point from the average of the data set and the ratio of the first and second value comprises a representation of blood pressure variation. Comparator 20 compares the calculated ratio with a threshold value to provide a comparison indicator. Patient monitor 19, in response to the comparison indicator indicating the ratio exceeds the threshold value, generates an alert message associated with the threshold.

System 10 uses blood pressure measurements to track and monitor patient vital signs and health status. For invasive blood pressure, the systolic and diastolic pressure are acquired each beat. While in NIBP measurement, the systolic and diastolic pressures are obtained in 2 minute intervals, for example, since air inflation and deflation takes time. So together with discrete pressure measurement, the pressure variability and variation is used to track a trend and detect patient pathologies and events.

Figure 2:
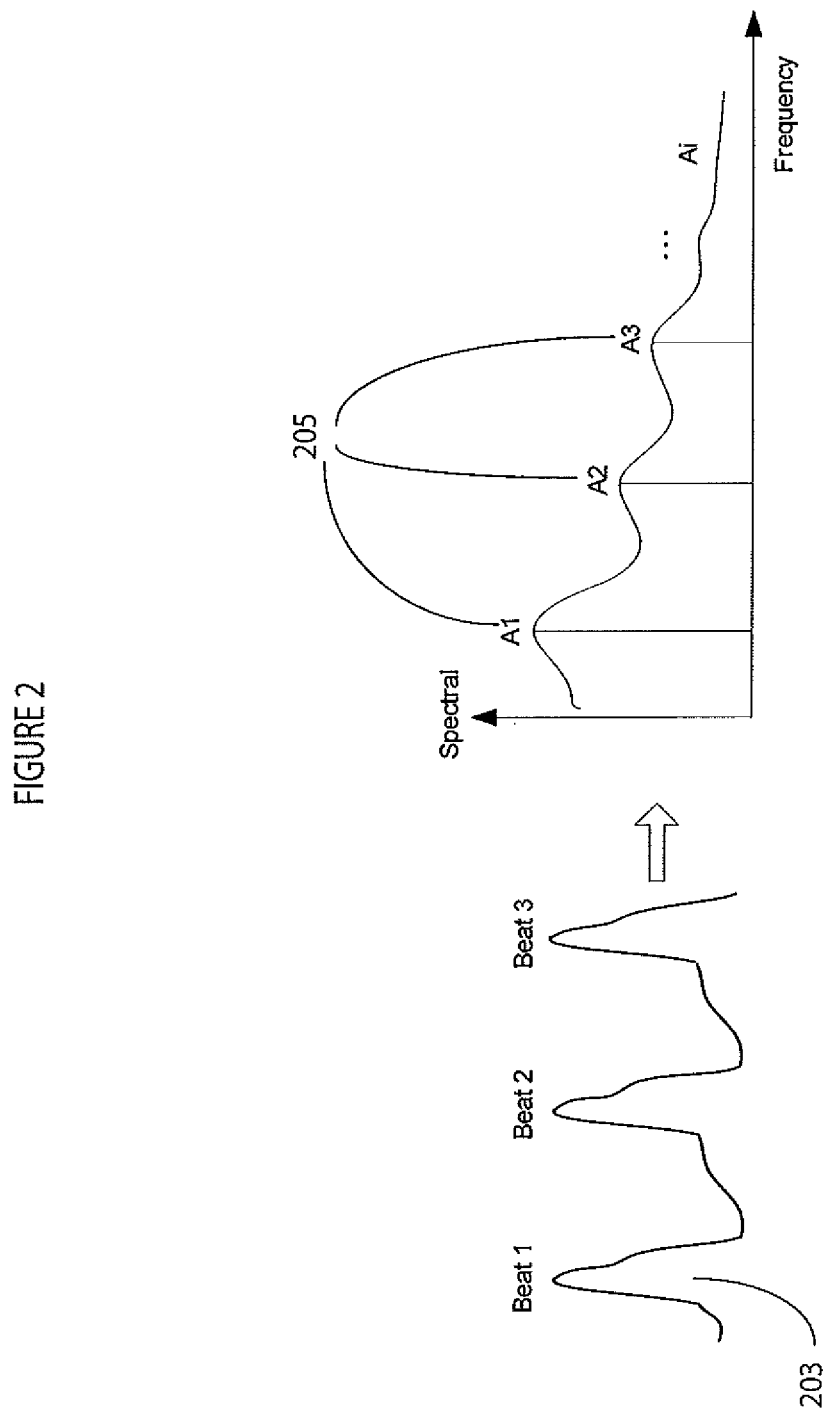
FIG. 2 illustrates spectral analysis of a continuous pressure waveform and data series and variation characterization, according to invention principles.

FIG. 2 illustrates spectral analysis of a continuous pressure waveform and data series and variation characterization. System 10 analyzes a blood pressure signal waveform of an individual heart beat cycle (e.g., 203) to determine a spectrum and pressure variation by averaging signal data of multiple heart beat signals to improve noise immunity. Similarly, other types of modeling methods and approaches may be used by system 10 for data analysis. Discrete or continuous blood pressure measurements may be modeled based on an AR (Autoregression) model, Autoregression and Moving Average (ARMA) model, and a Gaussian distribution. Definitions.

A discrete data series, such as of systolic and diastolic pressures, $A_i$ is a blood pressure measurement data series (discrete pressure measurements and data values), $E(\bullet)$ is the expectation of the data series and $\mu$ is the standard deviation of the data series, and the pressure measurement variation is, $$\text{pressure\_variation}_{Discrete} = \frac{E(A_i)}{\mu}.$$

A continuous data set, $B_i$ comprises sample data of a continuous blood pressure waveform (such as in invasive pressure measurement), $f_B$ is the spectrum of the blood pressure waveform data (for each heart cycle), the local maximum peak values of $f_B$ are $A_1, A_2, A_3$, respectively (205 FIG. 2) and continuous pressure variation is, $$\text{pressure\_variation}_{Continuous\_1} = \frac{|A_1|}{|A_2|}$$

$$\text{pressure\_variation}_{Continuous\_2} = \frac{|A_1 - A_2|}{|A_2 - A_3|}, \ldots$$

Figure 3:
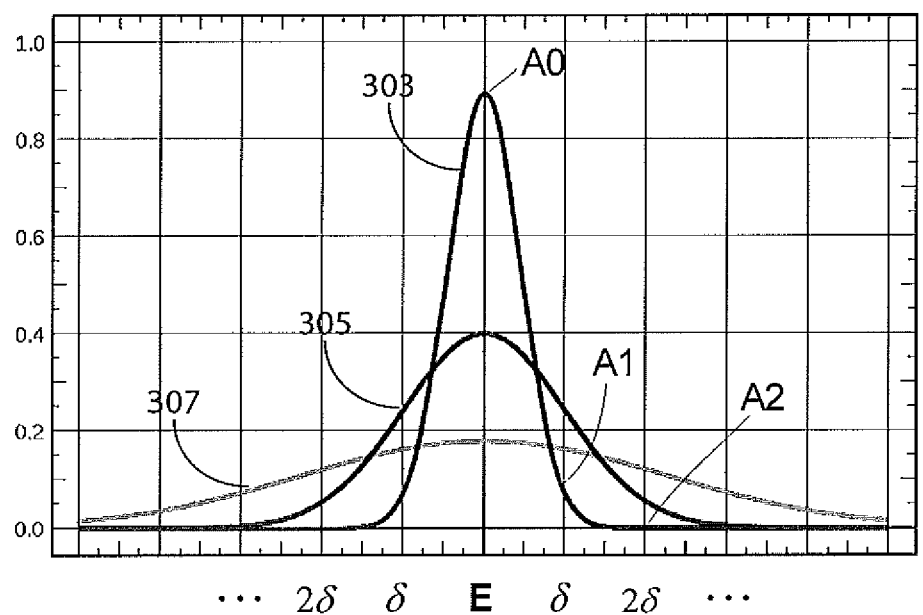
FIG. 3 shows Gaussian modeling based blood pressure pattern analysis and variability calculation, according to invention principles.

FIG. 3 illustrates Gaussian modeling based blood pressure pattern analysis and variability calculation. System 10 uses blood pressure data to generate a Gaussian modeling curve (e.g., curve 303) for blood pressure pattern analysis. System 10 (FIG. 1) performs statistical modeling and data matching using a Gaussian curve matching and modeling function, for example, $$\text{Gaussian normal distribution} = \frac{1}{\delta\sqrt{2\pi}} e^{-(x-E)^2/(2\delta^2)}$$

System 10 calculates modeling based blood pressure variability using, $$\text{First order variability} = \frac{A0}{A1}$$

$$\text{Second order variability} = \frac{A0 - A1}{A1 - A2}$$

In which, A0 is the curve magnitude at an expectation point, A1, A2, . . . are the modeling curve magnitude at different deviation (e.g., standard deviation) points, such as $\delta, 2\delta, \ldots$ as illustrated in curve 303 of FIG. 3. Different curves 303, 305 and 307 represent different modeling results based on the cardiac blood pressure measurements and reflects statistical pattern change and variability of blood pressure data. Hence by calculating and quantifying blood pressure variability, patient health status, such as cardiac tissue and function abnormality, is detected and characterized. System 10 performs high order statistical variability analysis for blood pressure modeling and calculation by comparison of variability data with an abnormality evaluation threshold. In an example, blood pressure data in a heart beat window is processed by system 10 to provide a Gaussian model in which A0, A1, A2, . . . , represent different statistical values in a modeling curve e.g., curve 303. In response to receiving blood pressure data of a successive heart beat cycle, system 10 adaptively uses data of the new successive cycle to update the model and curve. Thereby system 10 provides a different data set for each different window for real time curve calculation and for determination of $A0_i, A1_i, A2_i, \ldots$.

Figure 4:
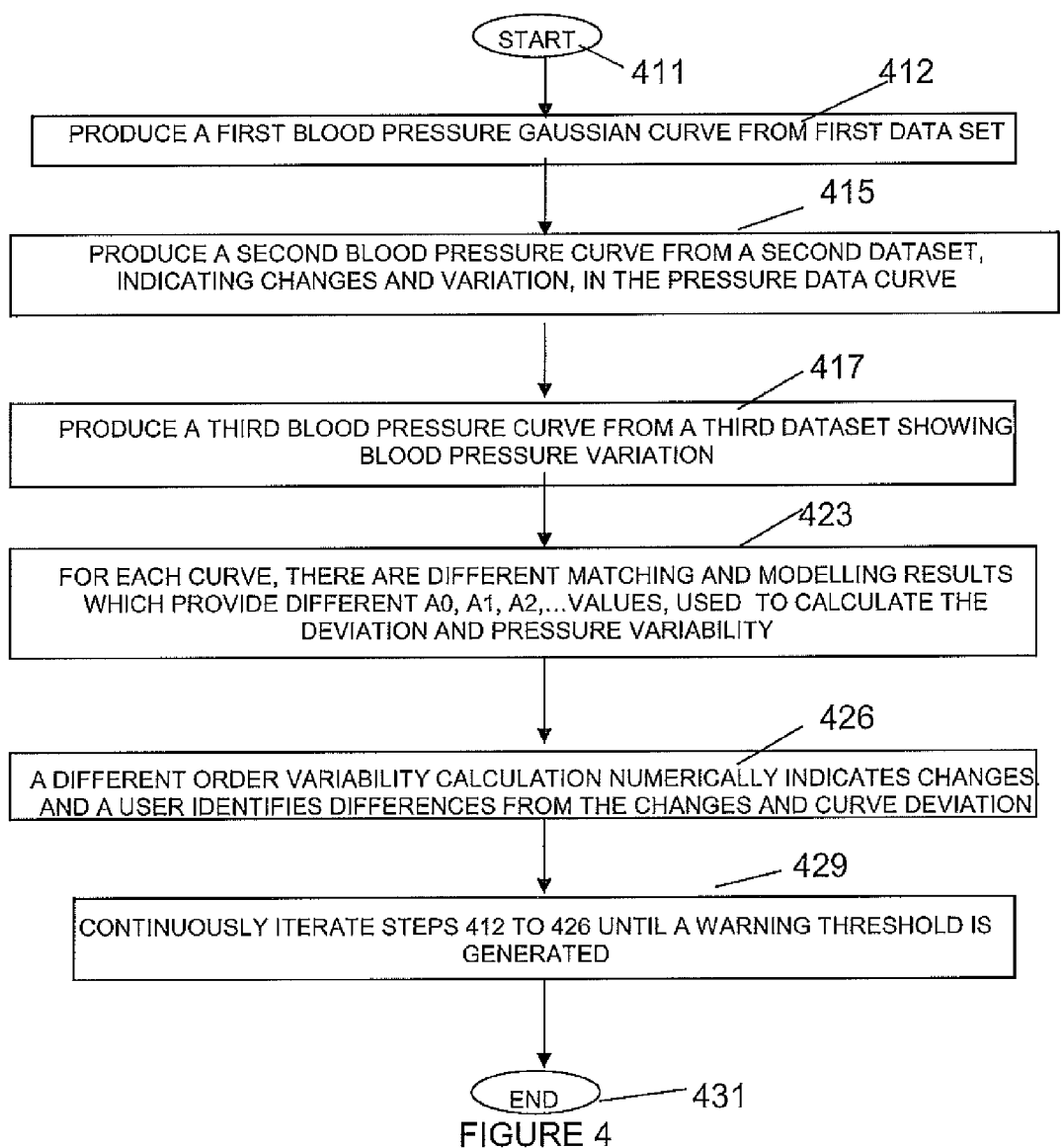
FIG. 4 shows a flowchart of a process performed by the system for blood pressure data based patient health status and pathology detection and diagnosis, according to invention principles.

FIG. 4 shows a flowchart of a process performed by the system for blood pressure data based patient health status and pathology detection and diagnosis. System 10 in step 412 following the start at step 411, generates a first Gaussian blood pressure curve (e.g., curve 303 FIG. 3) from a first data set. System 10 in step 415, generates a second blood pressure curve (e.g., curve 305 FIG. 3) from a second data set. Curve 305 indicates changes and variation from curve 303 in the pressure data curve. System 10 in step 417, generates a third blood pressure curve (e.g., curve 307 FIG. 3) from a third data set. Curve 307 indicates changes in the variation from curve 303. A data set of blood pressure measurements, a1-an, is mapped to Gaussian curve 303 and based on the curve, A0, A1, A2 . . . An values are derived according to standard deviation level, $\delta, 2\delta, \ldots$.

In step 423, system 10 determines different modeling result values of A0, A1, A2, etc., for curves 303, 305 and 307 that are used to calculate deviation and pressure variability. In step 426, system 10 determines different variability values of different level as follows. Higher order variability functions can also readily be derived in the series and used for the blood pressure analysis.

$$\text{First order variability} = \frac{A0}{A1}$$

$$\text{Second order variability} = \frac{A0 - A1}{A1 - A2}$$

$$\text{Higher order example} = \left|\frac{(A0 - A1) - (A1 - A2)}{(A1 - A2) - (A2 - A3)}\right|.$$

System 10 also calculates values employing high order statistical theories. System 10 maps a blood pressure input data set to a curve as output such as curves as illustrated in FIG. 3 having a data distribution including A0, A1, A2 values. The variation calculation based on A0, A1, A2, indicates blood pressure changes so that if there is an unexpected change, the data modeling curve changes and the curve model switches from curve 303 to 305, for example. The calculated amplitude and deviation change values indicate pressure status change and quantifies curve mode changes. A user identifies differences from the curve changes and the calculated different order variability values that numerically indicates changes. In step 429, system 10 iteratively repeats steps 412 to 426 until a warning threshold is exceeded. The process of FIG. 4 ends at step 431.

Figure 5:
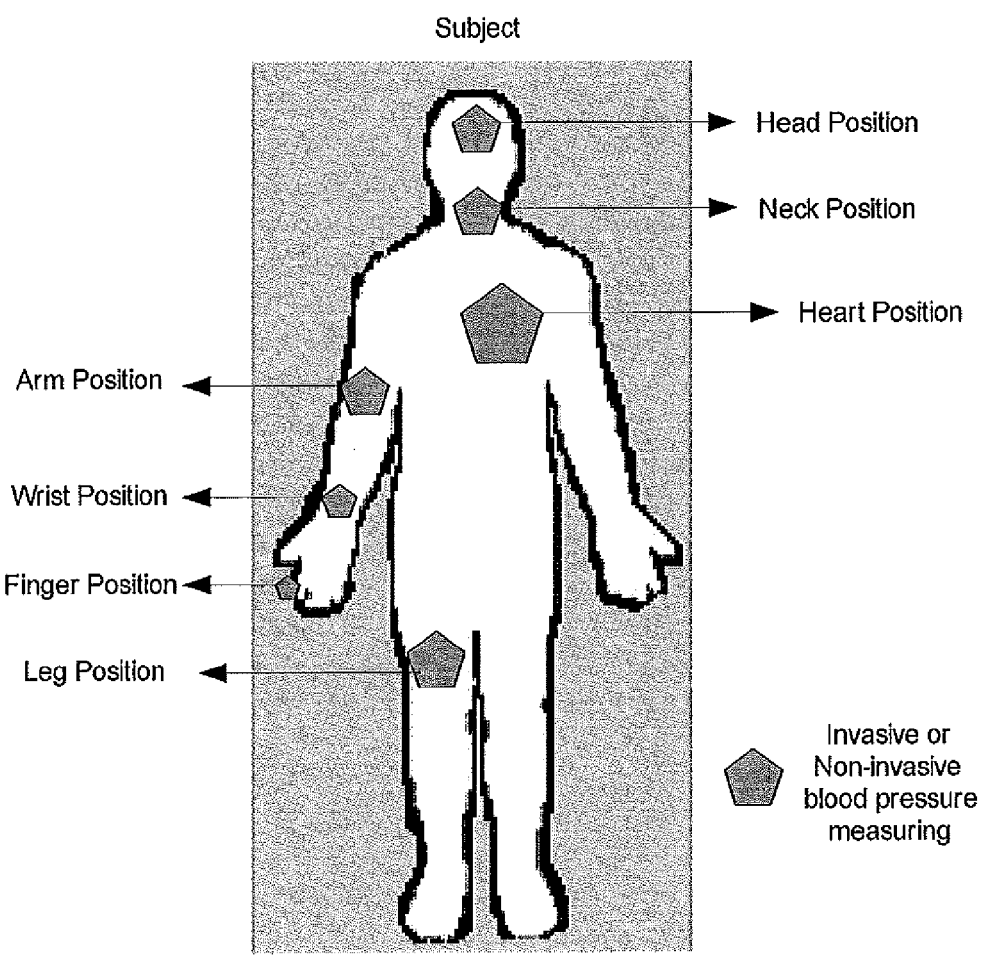
FIG. 5 shows different anatomical positions used for invasive or non-invasive methods for sensing hemodynamic and blood pressure signals, according to invention principles.

FIG. 5 shows different anatomical positions including, head, neck, heart, arm, wrist, finger and leg positions, used for invasive or non-invasive methods for sensing hemodynamic and blood pressure signals. System 10 uses a selectable kind of invasive or non-invasive blood pressure sensor or transducer employing different kinds of data sensing and acquisition method based on the anatomical position at which blood pressure is being measured. For example, for a heart position, ultrasound and electromagnetic field methods may be used whereas lasers may be utilized in signal acquisition and monitoring for a finger position. For wrist and arm positions, different methods are selected based on measuring convenience, including ultrasound and vibration sensing based hemodynamic signal monitoring. Pressure at different sites may be measured non-invasively or invasively. Intracranial blood pressure data may be acquired in a head and neck, for example. System 10 calculates blood pressure variation values to facilitate earlier detection of abnormality at different anatomical positions, such as artery, vein and capillary positions to prevent fatal disease, such as a brain hemorrhage. System 10 analyzes variation in acquired pressure data (such as a systolic and diastolic value series) at different anatomical positions to detect and characterize a blood pressure pattern and determine a blood pressure trend to identify patient pathologies and clinical events and identify location, timing, severity and type of cardiac pathology. The analysis may also involve statistical analysis such as a hypothesis test and entropy analysis.

Figure 6:
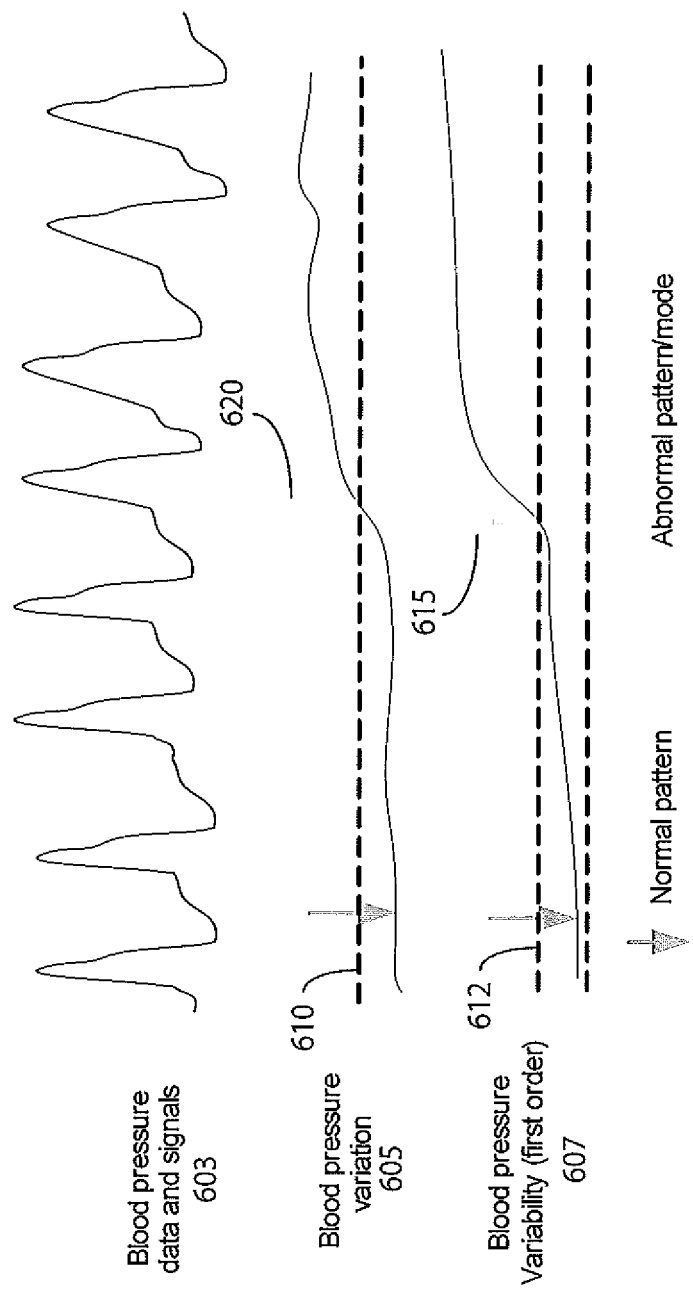
FIG. 6 shows simulation of data variation for blood pressure monitoring and diagnosis for patient health status determination and tracking, according to invention principles.

FIG. 6 shows simulation of blood pressure data variation for patient health status determination and tracking. System 10 (FIG. 1) processes invasive blood pressure waveform 603 for variation based blood pressure abnormality detection to derive pressure variation waveform 605 and pressure variability first order waveform 607 (using the functions previously described). System 10 determines abnormality at point 620 in the pressure variation waveform 605 in response to the variation waveform exceeding predetermined (+15% above normal range) threshold 610. System 10 determines abnormality at point 615 in the pressure variability waveform 607 in response to the variation waveform exceeding predetermined (+10% above normal range) threshold 612. In addition, system 10 adaptively acquires blood pressure data at different anatomical positions (including non-invasive and invasive positions) for comparison to improve determining a location of an abnormal vessel or tissue, for example. In certain diseases, one heart chamber (such as a left ventricle) may not work at normal squeezing speed, which may slow down a diastolic time period (including time length, pressure amplitude, period between EoS (End of Systolic) time to diastolic pressure time, rate of pressure change dP/dt). System 10 detects these changes by analyzing a blood pressure waveform.

System 10 blood pressure variation and variability analysis adaptively and automatically selects a pressure parameter and analysis function in response to data indicating patient medical history and medical conditions. System 10 uses a single pressure or combined pressures of different types or from different anatomical sites in variation analysis. The pressure types include systolic pressure, diastolic pressure, mean pressure, EOS (end of systolic) pressure, EOD (end of diastolic) pressure, maximum blood pressure and minimum blood pressure. System 10 adaptively selects a calculation method such as a continuous or discrete variation calculation method, first order or higher order variability analysis, different models for data modeling (such as AR, ARMA, Gaussian) in response to data indicating a clinical application, for example. System 10 also enables a user to select a calculation method for blood pressure variation analysis.

System 10 continuously monitors blood pressure in order to detect and characterize changes in blood pressure for differentiation of medical conditions. Blood pressures from multiple different anatomical sites may be used for analysis and the different pressures are dynamically selected for calculation in response to a type of clinical application. In an example, a blood pressure (systolic) value data set has 5 measurements (a data set comprises a calculation window size of 5-10 heart cycles, for example). The data set comprises, benign signals (reference values, 120, 116, 122, 123 and 128 and ongoing pressure measurement values 128, 137, 126, 111 and 109. System 10 calculates an average and standard deviation value of average E=121.8, standard deviation u=4.38 for benign signals and E=122.2, u=11.91 for ongoing signals. The data indicates variation in the ongoing measurement and system 10 uses Gaussian modeling to derive data distribution related parameters (using normalized amplitude in a distribution) comprising A0=0.83, A1=0.32, A1=0.16 for the benign signal data set and comprising A0=0.68, A1=0.43, A1=0.29 for the ongoing pressure measurement data set.

System 10 uses the Gaussian modeled data to calculate first order variability=2.6 and second order variability=3.2 for benign signals and first order variability=1.58 and second order variability=1.79 for ongoing signals. The variability calculation indicates both first order and second order variation of the ongoing signal have changed more than 20% from the corresponding benign signal (pressure) data set variation. System 10 generates a warning in response to systolic pressure variability exceeding a predetermined threshold range (or a change in variation direction) indicating a potential cardiac event or condition.

Figure 7:
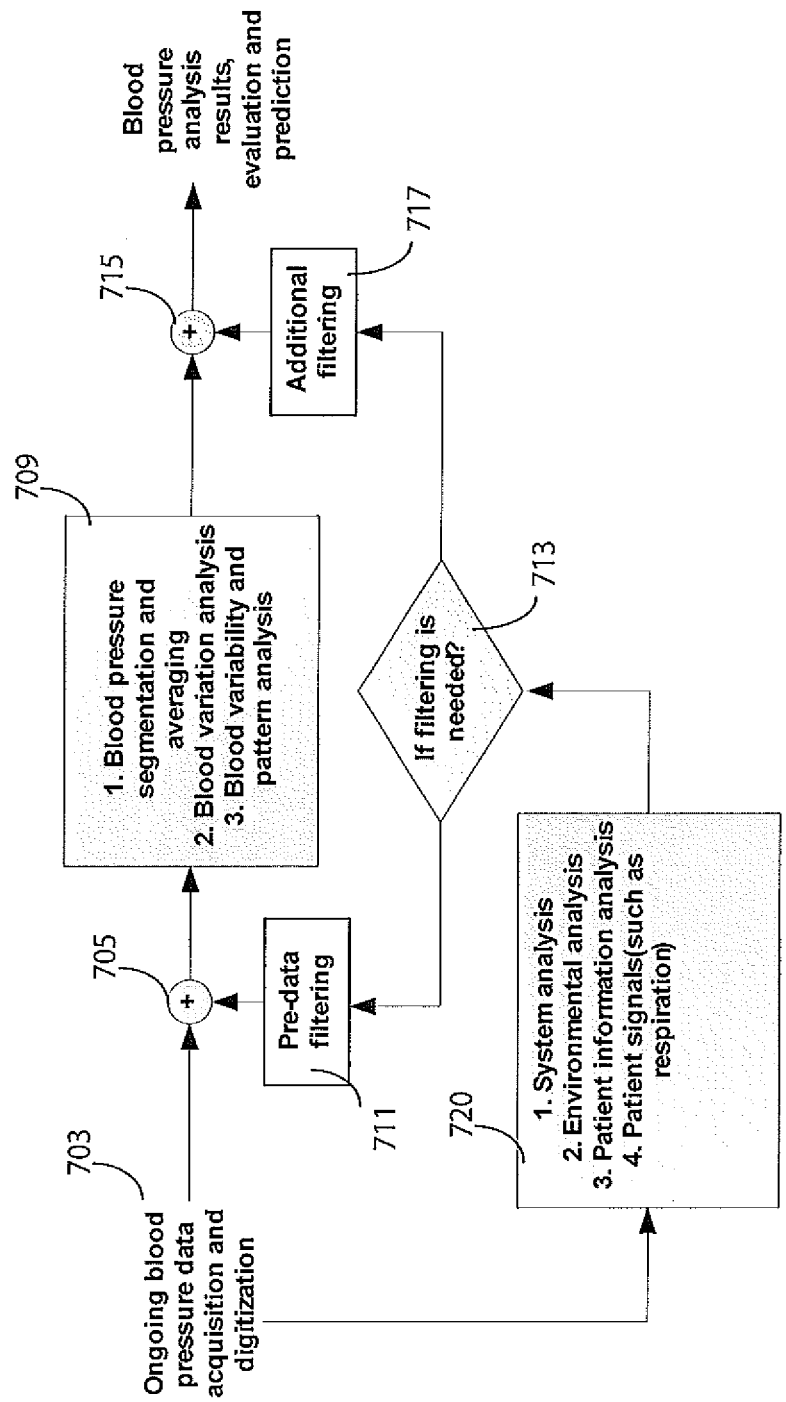
FIG. 7 shows a flowchart of a process for adaptive filtering of blood pressure signals for blood pressure data series variation and variability analysis, according to invention principles.

FIG. 7 shows a flowchart of a process for adaptive filtering of blood pressure signals for blood pressure data series variation and variability analysis. Blood pressure signal distortion may be caused by medical device noise and patient noise (respiration and movement), for example. In order to achieve better blood pressure analysis, system 10 adaptively filters a blood pressure signal based on patient context and noise for subsequent analysis to determine blood pressure changes caused by drug delivery, clinical events, and patient health status (e.g. cardiac tissue distortion, function changes). System 10 adaptively selects a filtering method in response to type of noise present such as electrical noise needing 50/60 notch filtering, respiration needing high pass filtering, patient movement needing singularity artifacts suppression. After pre-filtering and data analysis, other filtering may be used for singularity cleaning and shape filtering. The system filters multiple hemodynamic signals, such as invasive blood pressure signals from a blood pressure catheter, a NIBP signal, and signals derived from other invasive or less invasive methods for blood pressure acquisition.

System 10 in step 709 following summation filter stage 705, segments and averages blood pressure signal data that was acquired and digitized in step 703, performs variation and variability and pattern analysis on one or more heart cycles and heart cycle segments of the data and averages results over multiple cycles. The resultant data is output following a further summation filter stage 715. System 10 in step 713 determines whether filtering is to be applied at stage 705 and/or stage 715 based on noise content in particular frequency ranges of the blood pressure signal such as power line frequency and respiratory frequency determined by a noise analysis performed in step 720. System 10 also determines the type of filtering to be applied to the blood pressure signal based on the analysis performed in step 720. The analysis of step 720 determines from other patient signals (such as a respiration signal, vital sign signal), patient record information and data indicating system and environment information what frequency ranges need to be filtered with notch, low and high pass filters, for example. The filtering is performed at one or more of summation stages 705 and 715 using pre-data filter unit 711 and additional filtering unit 717, respectively.

Figure 8:
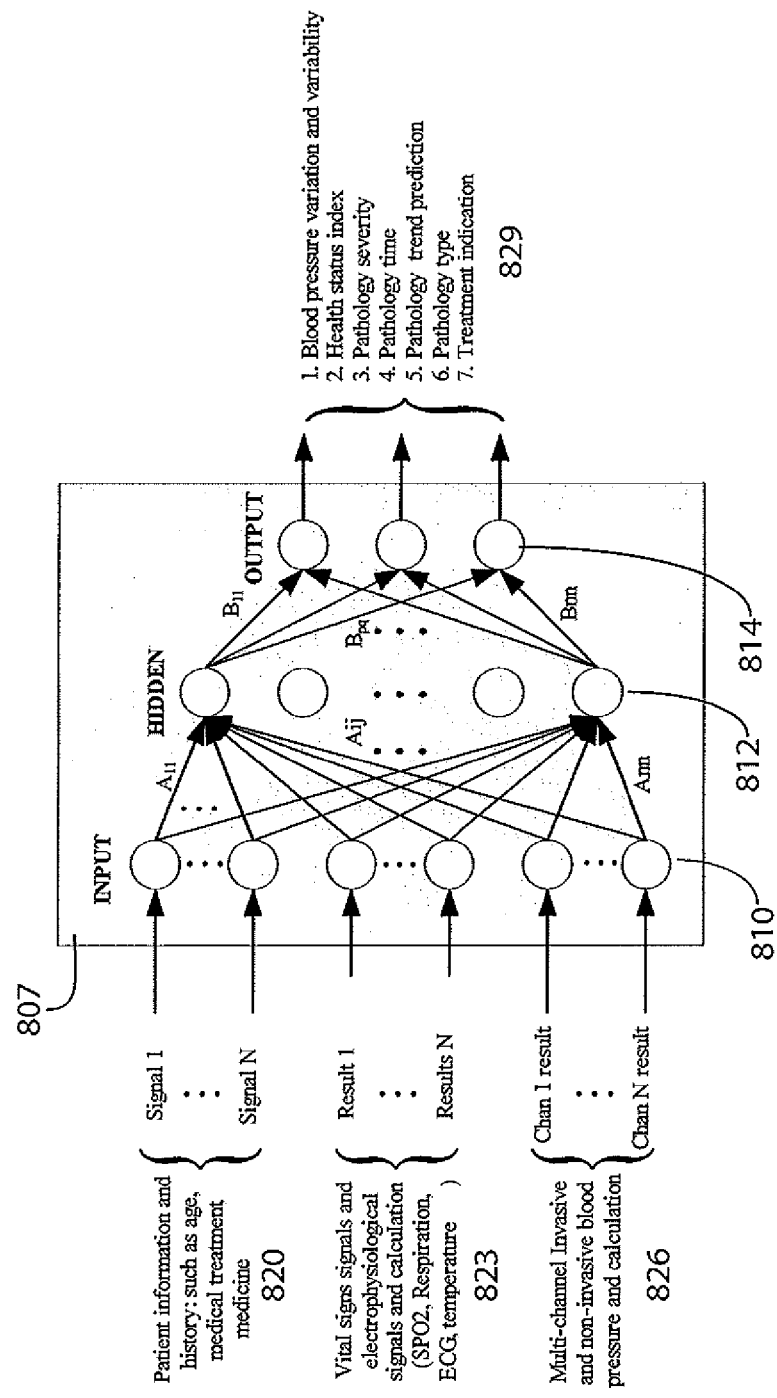
FIG. 8 shows an artificial neural network (ANN) used for heart performance characterization and abnormality detection, according to invention principles.

FIG. 8 shows an artificial neural network (ANN) system 807 used for heart performance characterization and abnormality detection. ANN unit 807 employs blood pressure data series variation analysis to identify cardiac disorders. ANN unit 807 maps patient medical record data (age, treatment, medication) 820, electrophysiological signal amplitude and frequency related parameters and vital sign data (including respiration, ECG, temperature and blood oxygen saturation) 823 and multi-channel invasive and non-invasive blood pressure signal data values 826, to output parameters 829. Output parameters 829 include blood pressure variation values, a patient health status index and location, a pathology severity indicator, a time of a cardiac event, a pathology trend indication, a pathology type indication and candidate treatment suggestions. ANN unit 807 structure comprises 3 layers, an input layer 810, hidden layer 812 and output layer 814. ANN unit $A_{ij}$ weights are applied between input layer 810 and hidden layer 812 components of the ANN computation and $B_{pq}$ weights are applied between hidden layer 812 and calculation index components 814 of the ANN computation. The $A_{ij}$ weights and $B_{pq}$ weights are adaptively adjusted and tuned using a training data set. ANN unit 807 incorporates a selflearning function that processes signals 820, 823 and 826 to increase the accuracy of calculated results.

ANN unit 807 maps input signals 820, 823 and 826 to a candidate diagnosis or treatment suggestion 829 to localize a tissue impairment within an organ and determine time of occurrence within a heart cycle. ANN unit 807 also identifies arrhythmia type (e.g., AF, MI, VT, VF), severity of arrhythmia treatment and urgency level and is usable for automatic heart condition detection, diagnosis, warning and treatment. Further unit 807 performs statistical analysis to construct a threshold used to detect tissue impairment and diagnose and predict cardiac arrhythmia and pathology.

Following a training phase with a training data set, ANN unit 807 maps signals 820, 823 and 826 to data 829 indicating an Arrhythmia type, Arrhythmia severity, candidate treatment suggestions, localized tissue impairment information identifying the cardiac arrhythmia position, pathology conducting sequence, abnormal tissue area and focus of the disorder and irregularity, for example. The severity threshold of a pathology mapping decision may vary from person to person and is adjusted at the beginning of analysis. The system may be advantageously utilized in general patient monitoring and implantable cardiac devices for real time automatic analysis and detection of cardiac arrhythmias and abnormalities.

Figure 9:
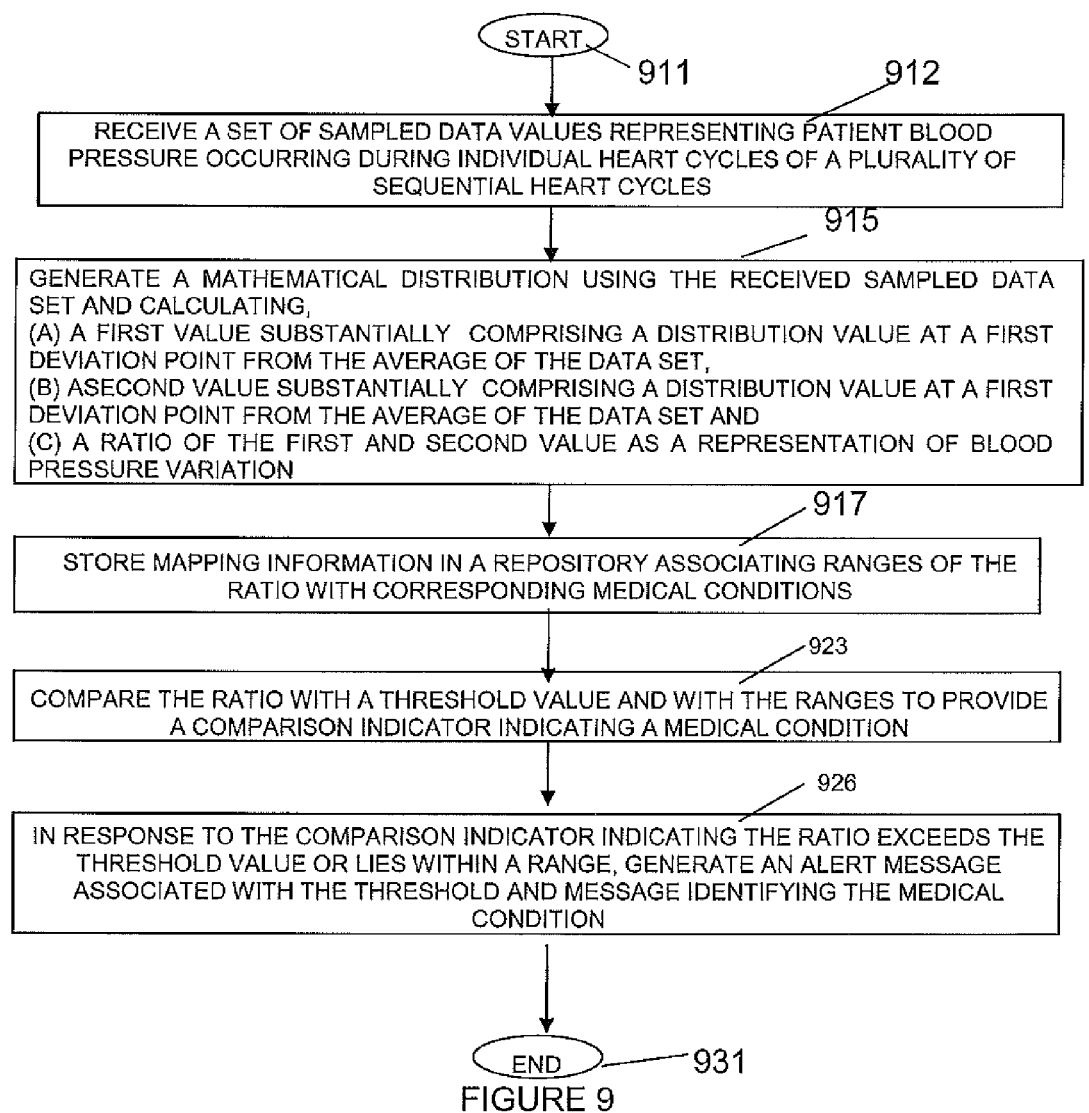
FIG. 9 shows a flowchart of a process used by a system for heart performance characterization and abnormality detection, according to invention principles.

FIG. 9 shows a flowchart of a process used by system 10 for heart performance characterization and abnormality detection. In step 912 following the start at step 911, interface 12 receives a set of sampled data values representing patient blood pressure occurring during individual heart cycles of multiple sequential (e.g., successive) heart cycles. The blood pressure comprises at least one of, (a) an intra-cardiac blood pressure, (b) a systolic blood pressure, (c) a diastolic blood pressure, (d) an invasive blood pressure and (e) a non-invasive blood pressure. Signal processor 15 in step 915 generates a mathematical distribution using the received sampled data set and calculates, (a) a first (e.g., amplitude) value substantially comprising a distribution value at a first deviation point from the average of the data set, (b) a second (e.g., amplitude) value substantially comprising a distribution value at a first deviation point from the average of the data set and (c) a ratio of the fast and second value as a representation of blood pressure variation. In one embodiment, the average of the sampled data set comprises one of, (a) an arithmetic mean, (b) a median and (c) a root mean square value and the second value substantially comprises a standard deviation value of the dataset. The mathematical distribution comprises one of, (a) a Gaussian distribution, (b) a normal distribution, (c) an Autoregression distribution model and (d) an Autoregression and Moving Average distribution model, for example. Further, in one embodiment, the mathematical distribution comprises a spectrum, the first value substantially comprises a frequency spectrum value at a first peak point and the second value substantially comprises a frequency spectrum value at a second peak point.

Signal processor 15 also generates a third value substantially comprising a distribution value at a second deviation point from the average of the data set. The second deviation point is substantially twice the deviation from the average of the data set as the first deviation point. Processor 15 generates a ratio of a difference between the first and second values and a difference between the second and third values as representation of blood pressure variation.

In step 917 processor 15 stores in repository 17 predetermined mapping information associating predetermined ranges of the ratio with corresponding medical conditions. The predetermined mapping information associates ranges of the ratio with particular patient demographic characteristics and with corresponding medical conditions. Comparator 20 in step 923 compares the ratio with a threshold value and with the ranges to provide a comparison indicator indicating a medical condition. The system uses patient demographic data including at least one of, age weight, gender and height in comparing the ratio with the ranges and generating an alert message indicating a potential medical condition. The threshold value is derived from recorded blood pressure data for the patient or for a population of patients having similar demographic characteristics including (a) age, (b) weight, (c) gender and (d) height, to those of the patient. Signal processor 15 dynamically adjusts the threshold value in response to a determined blood pressure variation of the patient. In step 926, in response to the comparison indicator indicating the ratio exceeds the threshold value or lies within one of the ranges, patient monitor 19 generates an alert message associated with the threshold and identifying the medical condition. The process of FIG. 9 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor.

The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system performs blood pressure variation analysis involving analyzing different pressure values to provide information for cardiac status and event detection and interpretation. Further, the processes and applications may, in alternative embodiments, be located on one or more (e.g., distributed) processing devices on a network linking the units of FIG. 1. Any of the functions and steps provided in FIGS. 1-9 may be implemented in hardware, software or a combination of both.

What is claimed is:

1. A system for heart performance characterization and abnormality detection, comprising:
   an interface configured to receive a set of raw sampled data values representing patient blood pressure occurring during individual heart cycles of plurality of sequential heart cycles;
   a signal processor configured to generate a mathematical distribution directly using the received raw sampled data set and calculate,
      (a) a first value substantially comprising an average of the raw sampled data set,
      (b) a second value substantially comprising a magnitude value of said distribution at a first deviation point from the average of the raw sampled data set and
      (c) a ratio of the first and second values as a representation of blood pressure variation; and
   a comparator configured to compare said ratio with a threshold value to provide a comparison indicator; and
   a patient monitor configured to, in response to said comparison indicator indicating said ratio exceeds the threshold value, generate an alert message associated with the threshold.

2. A system according to claim 1, wherein said plurality of sequential heart cycles are successive heart cycles.

3. A system according to claim 1, wherein said average of the raw sampled data set comprises at least one of, (a) an arithmetic mean, (b) a median, and a (c) a root mean square value.

4. A system according to claim 1, wherein said first deviation point substantially comprises a standard deviation value of the dataset.

5. A system according to claim 1, wherein said signal processor generates a third value substantially comprising a distribution value at a second deviation point from the average of the data set.

6. A system according to claim 5, wherein said signal processor generates a ratio of a difference between the first and second values and a difference between the second and third values as representation of blood pressure variation.

7. A system according to claim 5, wherein said second deviation point is substantially twice the deviation from the average of the data set as the first deviation point.

8. A system according to claim 1, wherein said blood pressure comprises at least one of, (a) an intra-cardiac blood pressure, (b) a systolic blood pressure, (c) a diastolic blood pressure, (d) an invasive blood pressure and (e) a non-invasive blood pressure.

9. A system according to claim 1, wherein
   said comparator determines a comparison indicator indicating whether said ratio lies in a predetermined value range and
   said patient monitor, in response to said comparison indicator indicating said ratio lies in a predetermined value range, generates an alert message associated with the value range.

10. A system according to claim 1, wherein said threshold value is derived from recorded blood pressure data for said patient.

11. A system according to claim 1, wherein said threshold value is derived from recorded blood pressure data for a population of patients having similar demographic characteristics including at least two of, (a) age, (b) weight, (c) gender and (d) height, to those of said patient.

12. A system according to claim 1, wherein said signal processor dynamically adjusts said threshold value in response to a determined blood pressure variation of said patient.

13. A system according to claim 1, wherein said mathematical distribution comprises at least one of, (a) a Gaussian distribution, (b) a normal distribution, (c) an Autoregression distribution model and (d) an Autoregression and Moving Average distribution model.

14. A system according to claim 1, including
   a repository of predetermined mapping information, associating ranges of the ratio with corresponding medical conditions and
   said comparator compares said ratio with said ranges to provide a comparison indicator identifying a medical condition and
   said patient monitor generates an alert message identifying said medical condition.

15. A system according to claim 14, wherein said predetermined mapping information associates ranges of the ratio with particular patient demographic characteristics and with corresponding medical conditions and said system uses patient demographic data including at least one of, age weight, gender and height in comparing the ratio with said ranges and generating an alert message indicating a potential medical condition.

16. A system according to claim 1, wherein said first value and said second value comprise amplitude values.

17. A method employed by at least one processing device for heart performance characterization and abnormality detection, comprising:
   receiving a set of raw sampled data values representing patient blood pressure occurring during individual heart cycles of plurality of sequential heart cycles;
   generating a mathematical distribution directly using the received raw sampled data set and calculating,
      (a) a first value substantially comprising an average of the raw sampled data set,
      (b) a second value substantially comprising a magnitude value of said distribution at a first deviation point from the average of the raw sampled data set and (c) a ratio of the first and second values as a representation of blood pressure variation; and comparing said ratio with a threshold value to provide a comparison indicator; and in response to said comparison indicator indicating said ratio exceeds the threshold value, generating an alert message associated with the threshold.

18. A method employed by at least one processing device for heart performance characterization and abnormality detection, comprising the activities of:

receiving a set of sampled data values representing patient blood pressure occurring during individual heart cycles of a plurality of sequential heart cycles;

generating, from the received sampled data set, a spectrum comprising spectral value against frequency and calculating, (a) a first local maximum peak value of the spectrum, (b) a second local maximum peak value of the spectrum, (c) a third local maximum peak value of the spectrum, (d) a first value substantially comprising a difference between the first and the second local maximum peak values, (e) a second value substantially comprising a difference between the second and the third local maximum peak values, (f) a ratio of the first and second values as a representation of blood pressure variation; and comparing said ratio with a threshold value to provide a comparison indicator; and in response to said comparison indicator indicating said ratio exceeds the threshold value, generating an alert message associated with the threshold.

* * * * *